United States Patent [19]

Brinkhoff

[11] 4,053,051
[45] Oct. 11, 1977

[54] EARPLUG PACKAGE AND METHOD OF MAKING IT

[75] Inventor: Carl H. Brinkhoff, Pittsburgh, Pa.

[73] Assignee: Mine Safety Appliances Company, Pittsburgh, Pa.

[21] Appl. No.: 721,948

[22] Filed: Sept. 10, 1976

[51] Int. Cl.² .............................................. A61F 11/02
[52] U.S. Cl. ..................................... 206/438; 53/167; 128/152
[58] Field of Search .................... 206/210, 363, 438; 128/151, 152; 53/3, 167

[56] References Cited

U.S. PATENT DOCUMENTS

| 2,268,536 | 12/1941 | Seidler | 206/363 |
| 2,393,340 | 1/1946 | Russell | 128/152 |
| 3,101,713 | 8/1963 | Sargent | 200/363 |
| 3,902,491 | 9/1975 | Lajus | 206/438 |
| 3,941,245 | 3/1976 | Oliverius | 206/438 |

Primary Examiner—William Price
Assistant Examiner—Joseph Man- Fu Moy
Attorney, Agent, or Firm—Brown, Murray, Flick & Peckham

[57] ABSTRACT

Extending into the open end of a cylindrical container is the stem of an earplug inserter that has an enlarged portion outside of the container forming a shoulder spaced from the open end of the container. Enclosing the stem between it and the encircling side wall of the container is a thin sound-attenuating mat of fibers, the marginal portion of which extends out of the container and flares outwardly across the inserter shoulder. This mat forms an earplug that is removable with the inserter from the container to permit insertion of the earplug in an ear by means of the inserter, which is then withdrawn from the plug. The earplug is made by placing a flat fibrous mat against the open end of the container and then pushing it into the container by means of the inserter stem.

8 Claims, 5 Drawing Figures

EARPLUG PACKAGE AND METHOD OF MAKING IT

It is an object of this invention to provide an inexpensive earplug package, in which an earplug is formed and protected until ready for use, in which the earplug is formed during its insertion in a container forming part of the package, and in which the earplug former is used for inserting the plug in an ear.

The invention is illustrated in the accompanying drawings, in which

Figure 1:
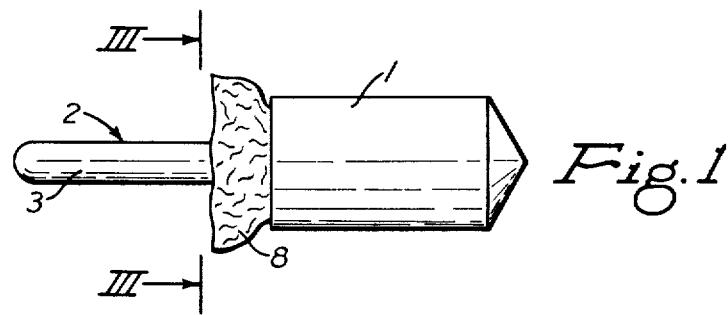
FIG. 1 is a side view of the package.
Figure 2:
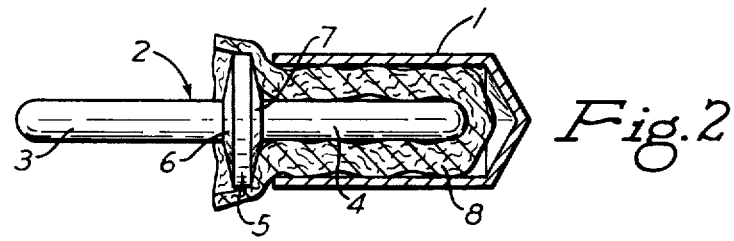
FIG. 2 is a longitudinal section.
Figure 3:
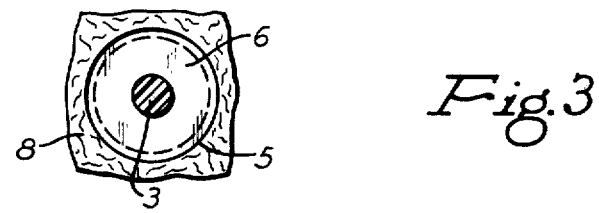
FIG. 3 is a cross section taken on the line III—III of FIG. 1.

Referring to FIGS. 1, 2 and 3 of the drawings, an earplug container 1 is formed from a suitable material, such as a plastic or cardboard, and is a hollow cylinder that may be closed at one end. An earplug inserter 2 has two substantially identical stems 3 and 4 aligned with each other and extending away from opposite sides of an enlarged central portion 5 of the inserter, the opposite sides of which form shoulders 6 and 7 extending around the two stems. Although these shoulders may be perpendicular to the longitudinal axis of the inserter, preferably they are inclined to the axis by tapering the enlarged portion outwardly away from the two stems. Each stem is considerably smaller in diameter than the inside diameter of the container. For example, the inner diameter of the container may be ⅝ inch while the diameter of each stem is ¼ inch. Thus, when one of the stems is centered in the container, the stem will be spaced ⅛ inch from the encircling wall of the container.

The earplug is made from a thin, sound-attenuating mat of fibers. The mat may have any desired shape, but to avoid waste of material in cutting it from a large sheet, it preferably is square. A 1⅜ inch square mat is adequate. It is a felted mat formed from fibers, which are finer than cotton and other natural fibers that are too coarse to provide good sound attenuation. A very suitable fiber for the earplug is a polypropylene fiber about two microns in diameter. However, if desired, glass fibers of about the same size and known as Swedish wool may be used. The mat should be about only 1/32 inch thick.

Figure 4:
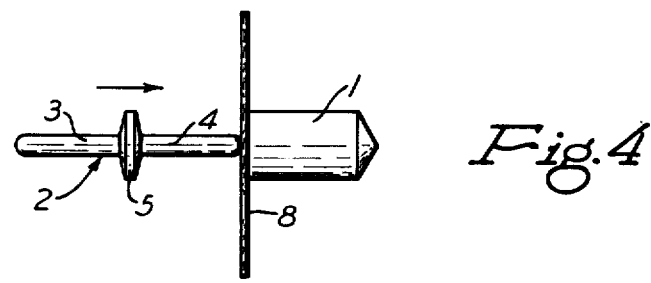
FIG. 4 is a reduced side view showing the earplug about to be formed.

In order to form the earplug, the fibrous mat 8 is placed against the open end of container 1 and centered on it, as shown in FIG. 4. Then, the rounded free end of one of the stems of inserter 2, such as stem 4, is pressed against the center of the mat and pushed into the container, the other stem serving as a handle or finger grip for holding the inserter. As the mat is pushed into the container, it is caused to fold out around stem 4 in the space between it and the encircling wall of the container, thereby enclosing the stem, with the free end of the stem pressed against the center of the mat, as shown in FIG. 3. The inserter is of such length that when it has been inserted the proper distance into the container, the enlarged portion 5 of the inserter will remain spaced from the open end of the container. With an inserter about 1⅛ inches long, each stem will be less than ⅜ inch long, and a stem will be inserted only about ⅜ inch into the container. The marginal portion of the mat extends out of the container and flares outwardly across the inserter shoulder 7 and may encircle the enlarged portion of the inserter, as shown in FIGS. 2 and 3.

The mat now is in the form of an earplug, which can be removed from the container with the inserter by pressing the exposed portion of the plug against the enlarged portion of the inserter with the fingers and pulling the plug and inserter out of the container together. Then the free stem 3 of the inserter is held in the fingers and the inserter is used to insert the plug in the ear, after which the inserter is pulled out of the plug and discarded. It will be seen that either stem can be used to form the plug by inserting it in the container. The action of inserting the inserter into the container forms the earplug, thereby avoiding having to go to the trouble and expense of first making an earplug, then mounting it on an inserter and then placing it in a container as is the case with the earplug in U.S. Pat. No. 2,393,340.

Figure 5:
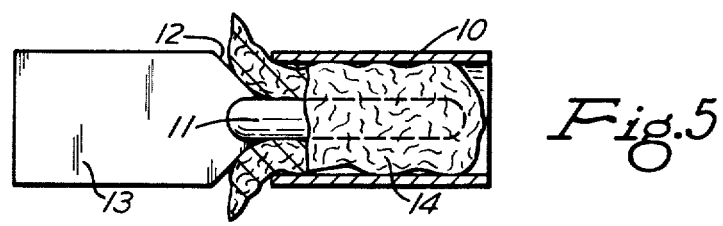
FIG. 5 is a longitudinal section of a modification.

In the modification shown in FIG. 5, both ends of the container 10 are open, but the outer end could be closed in the same way as the container in FIG. 1. The principal difference between this modification and the one described first is that the inserter has only one plug-forming stem 11. The entire portion of the inserter at the outer end of the stem is enlarged to form not only a shoulder 12 inclined away from the axis of the stem, but also to form the handle or finger grip 13 for the inserter. This grip may be cylindrical like the stem or thin and substantially flat. The earplug 14 is formed in the same way as described in connection with FIG. 4, and is inserted in the ear in the same way as first described.

According to the provisions of the patent statutes, we have explained the principle of our invention and have illustrated and described what we now consider to represent its best embodiment. However, we desire to have it understood that, within the scope of the appended claims, the invention may be practiced otherwise than as specifically illustrated and described.

I claim:

1. An earplug package comprising a cylindrical container open at at least one end, an earplug inserter having a stem extending axially into said open end of the container and spaced from the side wall of the container, the inserter having an enlarged portion outside of the container forming a shoulder extending laterally away from said stem and spaced from said open end of the container, and a thin sound-attenuating mat of fibers enclosing said stem and disposed between it and the encircling side wall of the container with the free end of said stem pressed against the central portion of the mat, the marginal portion of said mat extending out of the container and flaring outwardly across said shoulder, the mat forming an earplug removable with said inserter from the container to permit insertion of the earplug in an ear by means of the inserter.

2. An earplug package according to claim 1, in which said enlarged portion of the inserter is midway between the ends of the inserter, and the inserter has a second stem substantially identical to said first-mentioned stem projecting outwardly from the side of said enlarged portion opposite said shoulder, whereby either end of the inserter can extend into said container.

3. An earplug package according to claim 2, in which said enlarged portion of the inserter extends completely around said stem.

4. An earplug package according to claim 1, in which said enlarged portion of the inserter extends outwardly from said shoulder far enough to form a finger grip for holding onto the inserter.

5. An earplug package according to claim 4, in which said enlarged portion of the inserter is substantially flat and extends away from opposite sides of said stem.

6. An earplug package according to claim 1, in which said mat fibers are smaller in diameter than cotton fibers.

7. An earplug package according to claim 1, in which said mat fibers are polypropylene fibers substantially two microns in diameter.

8. The method of making an earplug package, comprising centering a thin fibrous mat over the open end of a cylindrical container, pressing the stem of an earplug inserter against the center of the mat and inserting the stem axially into the container to push the mat into it and cause the mat to enclose the stem, stopping insertion of the inserter into the container while the marginal portion of the mat remains outside of the container in a flared-out position between a shoulder on said inserter and the adjacent end of the container, whereby the mat forms an earplug that can be removed with the inserter from the container to permit insertion of the earplug in an ear by means of the inserter.

* * * * *